United States Patent
Divvela et al.

(10) Patent No.: US 7,485,726 B2
(45) Date of Patent: Feb. 3, 2009

(54) PROCESS FOR THE PREPARATION OF RISEDRONATE SODIUM HEMI-PENTAHYDRATE

(75) Inventors: Srinivasa Rao V. N Divvela, Hyderabad (IN); Lenin Racha, Hyderabad (IN); Sivakumaran Meenakshisunderam, Hyderabad (IN); Ramesh Dandala, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 25 days.

(21) Appl. No.: 11/653,556

(22) Filed: Jan. 16, 2007

(65) Prior Publication Data

US 2007/0173484 A1    Jul. 26, 2007

(30) Foreign Application Priority Data

Jan. 20, 2006   (IN)   ..................................... 94/2006

(51) Int. Cl.
*C07F 9/38*   (2006.01)
*C07D 213/30*   (2006.01)
(52) U.S. Cl. ....................................................... 546/22
(58) Field of Classification Search .................... 546/22
See application file for complete search history.

(56) References Cited

FOREIGN PATENT DOCUMENTS

WO    WO 2006/051553    *    5/2006

* cited by examiner

*Primary Examiner*—Charanjit S Aulakh
(74) *Attorney, Agent, or Firm*—Jay R Akhave

(57) ABSTRACT

The present invention relates to an improved process for the selective crystallization of 3-pyridyl-1-hydroxyethylidene-1,1-bisphosphonic acid sodium in pure hemi-pentahydrate form of Formula (I), by first converting 3-pyridyl-1-hydroxy-ethylidene-1,1-bisphosphonic acid into organic amine salt and then by replacing it with sodium salt.

19 Claims, No Drawings

PROCESS FOR THE PREPARATION OF RISEDRONATE SODIUM HEMI-PENTAHYDRATE

CROSS REFERENCE TO THE RELATED APPLICATION

This application claims the priority of Indian application no: 94/CHE/2006, filed on Jan. 20, 2006.

FIELD OF THE INVENTION

The present invention relates to an improved process for the selective crystallization of 3-pyridyl-1-hydroxyethylidene-1,1-bisphosphonic acid sodium in pure hemi-pentahydrate form of Formula (I), by converting 3-pyridyl-1-hydroxyethylidene-1,1-bisphosphonic acid into organic amine salt followed by replacing it with sodium salt.

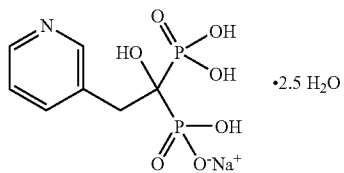

Formula I

BACKGROUND OF THE INVENTION

The bisphosponic acids and their pharmaceutically acceptable salts are an important class of medicaments that act as specific inhibitors of Osteoclast-mediated bone resorption and are useful in the treatment of bone disorders such as Paget's disease and osteoporosis. Bisphosphonates are synthetic analogs of pyrophosphate that bind to the hydroxyappetite found in the bone.

Bisphosphonates such as 3-pyridyl-1-hydroxyethylidene-1,1-bisphosphonic acid (Risedronate) have been proposed for use in the treatment of diseases of bone and calcium metabolism. Such diseases include osteoporosis, hyperparathyroidism, hypercalcemia of malignancy, ostolytic bone metastases, myosistis ossifcans progressiva, calcinoisis universalis, arthritis, neuritis, bursitis, tendonitis and other inflammatory conditions. At present Paget's disease and heterotropic ossification are successfully treated with both ethane-1-hydroxy-1,1-diphosphonic acid (EHDP) and Risedronate.

The bisphosphonates tend to inhibit the resorption of bone tissue, which is beneficial to patients suffering from excessive bone loss. However, in spite of certain analogies in biological activity, all bisphosphonates do not exhibit the same degree of biological activity. The salt and hydrate forms of bisphosphonates alter both their solubility and their bioavailability.

Bisphosphonates are capable of existing in several polymorphic or pseudopolymorphic forms. The polymorphs and pseudopolymorphs can be influenced by controlling the conditions under which the salt is obtained in solid form, for example by controlling conditions of crystallization. Solid-state physical properties that can differ from one polymorph (or pseudopolymorph) to the other include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate.

The above mentioned bisphosphonates were disclosed in U.S. Pat. No. 5,583,122, describing some of the bisphosphonate compounds like Risedronic acid and their pharmaceutical compositions comprising the said compounds.

It is known in the literature that Risedronate sodium exists in three hydration states: monohydrate, hemi-pentahydrate and anhydrous form. U.S. Pat. No. 6,410,520 describes selective crystallization of Risedronate sodium as a monohydrate or hemi-pentahydrate. The ratio of hemi-pentahydrate to monohydrate crystal forms in the product can be effectively controlled by varying the water to 3-pyridyl-1-hydroxyethylidene-1,1-bisphosphonic acid sodium ratio and isopropanol to water ratio as well as the temperature.

Further, U.S. '520 patent discloses, that the monohydrate and the hemi-pentahydrate are preferred forms and that the hemi-pentahydrate is the thermodynamically preferred crystalline form under processing conditions based on the observation that the monohydrate crystals convert to the hemi-pentahydrate form.

It is therefore desirable to provide an efficient process to selectively produce Risedronate sodium hemi-pentahydrate with high purity and high yield.

We have now found that, in the process of the present invention Risedronic acid is first treated with organic amine base to give Risedronate amine group followed by replacement of amine group with sodium ion producing Risedronate sodium in pure hemi-pentahydrate form in high yield and high purity.

OBJECTIVE OF INVENTION

The main objective of the present invention is to provide a simple and effective process for the preparation of Risedronate sodium in pure hemi-pentahydrate form of high purity on a commercial scale.

SUMMARY OF THE INVENTION

The present invention relates to an improved process for the preparation of 3-pyridyl-1-hydroxyethylidene-1,1-bisphosphonic acid sodium in pure hemi-pentahydrate form of Formula (I),

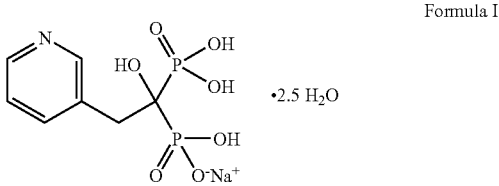

Formula I which comprises:

a) treating a compound of Formula (II),

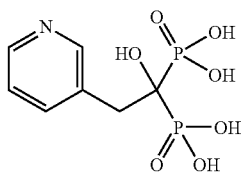

Formula II with an organic amine base in water to produce compound of Formula (III),

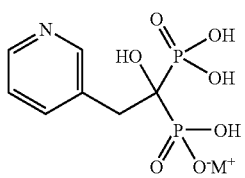

Formula III wherein $M^+$ is derived from organic amine base, b) treating a compound of Formula (III) with a base capable of giving sodium ions in a mixture of water and solvent to produce selectively 3-pyridyl-1-hydroxyethylidene-1,1-bisphosphonic acid sodium hemi-pentahydrate (I).

DETAILED DESCRIPTION OF THE INVENTION

The present invention relates to a selective crystallization of 3-pyridyl-1-hydroxyethylidene-1,1-bisphophonic acid sodium as hemi-pentahydrate, which comprises reacting 3-pyridyl-1-hydroxyethylidene-1,1-bisphophonic acid with an organic base selected from primary amines, such as cyclohexylamine, 2-ethylhexylamine, benzylamine, α-ethylbenzylamine and tert-octylamine, secondary amines, such as diethylamine, morpholine, dicyclohexylamine, N-methylbenzylamine or N,N'-dibenzylethylenediamine, tertiary amines, such as triethylamine, tributylamine, triisooctylamine, ethyldiisopropylamine, N-methylmorpholine, pyridine, 2,6-lutidine or quinoline, amidines, such as 1,5-diazabicyclo[4.3.0]non-5-ene or 1,8-diazabicyclo[5.4.0]undec-7-ene. A preferred base according to the invention is the triethylamine salt. The reaction is carried out in a protic solvent such as water, at a temperature ranging from −20° C. to +80° C., preferably from 0° C. to 40° C. The amount of base can be stoichiometric to the compound of Formula (II). The aqueous solution is filtered and washed with a solvent selected from ethyl acetate or ether. The resulting salt of the Formula (III) can be isolated by addition of an organic solvent selected from alcohols, esters, ethers, ketones, amides, nitriles or mixtures thereof. The preferred solvent is alcohol. The alcoholic solvent employed is selected from methanol, isopropyl alcohol, or mixtures thereof, preferably methanol.

Alternatively, one can also proceed directly for preparation of 3-pyridyl-1-hydroxyethylidene-1,1-bisphosphonic acid sodium hemi-pentahydrate without isolating compound of Formula (III) by adding sodium base selected from sodium methoxide, sodium ethanoate, sodium propanoate, sodium butanoate, sodium pentanoate, sodium 2-ethylhexanoate, sodium lactate, sodium acetate, or mixtures thereof, preferably sodium 2-ethylhexanoate, in a solvent selected from alcohols, esters, ethers, ketones, amides, nitrites or mixtures thereof. The base can be added as an aqueous solution or as a solution in solvent/water, or as a solid. The base can be added in one lot or in portions, or continuously depending upon the equipment being used. In one iteration, the ratio of solvent to water is adjusted to a ratio of from 20% to 60%. The sodium base can be stoichiometric to the compound of Formula (III) or in molar excess. The reaction is carried out at a temperature of about 10° C. to +60° C., preferably from 0° C. to 40° C. Isolating 3-pyridyl-1-hydroxyethylidene-1,1-bisphosphonic acid sodium as hemi-pentahydrate by conventional methods such as cooling to 0° C., filtering the solid and drying at 30° C. to about 45° C.

The following examples to prepare Risedronate sodium hemi-pentahydrate, will illustrate the nature of the invention and are provided for illustrative purpose only and should not be construed to limit the scope of the invention.

Preparation of
3-pyridyl-1-hydroxyethylidene-1,1-biphophonic acid sodium as hemi-pentahydrate

EXAMPLE 1

Triethylamine (7.71 g, 76.33 mmol) was added slowly to the 3-pyridyl-1-hydroxyethylidene-1,1-biphophonic acid (20 gm, 66.44 mmol) in DM water (200 ml) at 25-30° C., and the resulting solution was treated with carbon (0.2 g). The carbon was filtered. Methanol (250 ml) was added to the reaction mixture followed by 0.2 g of Risedronate sodium hemi-pentahydrate seed. Sodium 2-ethylhexanoate solution (14.3 g dissolved in 150 ml $CH_3OH$) was added to the reaction mixture in 20 min. The reaction was continued at 25-30° C. for 30 min and cooled to 5° C. and maintained for 2 hr. The product was filtered, washed with a mixture of methanol and water (1:1, 20 ml×2) and dried at 40-45° C. for 6 hr to obtain 16.4 g of Risedronate sodium hemi-pentahydrate.

EXAMPLE 2

Triethylamine (7.71 g, 76.33 mmol) was added slowly to the Risedronic acid (20 g, 66.44 mmol) in DM water (200 ml) at 25-30° C. The reaction mass was washed with ethyl acetate (80 ml×2). Methanol (250 ml) was added to the solution followed by addition of 0.2 g of seed material. Sodium-2-ethylhexanoate solution (14.3 g in 150 ml methanol) was added to the reaction mixture in 30 min and maintained for about 3 h at 25-30° C. The reaction mass was cooled to 5° C., the product was filtered and washed with mixture of methanol and water (1:1, 2×20 ml) and wet product was dried at 40-45° C. for 6 hr to obtain 16.6 g of Risedronate sodium hemi-pentahydrate.

We claim:

1. A process for the selective preparation of 3-pyridyl-1-hydroxyethylidene-1,1-bisphosphonic acid sodium in hemi-pentahydrate form of Formula (I),

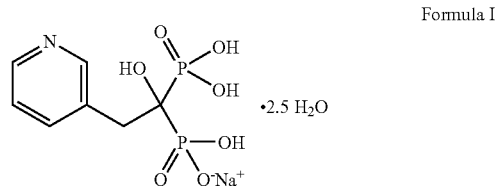

Formula I which comprises treating a compound of Formula III,

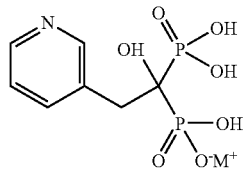

Formula III wherein M⁺ represents organic amine base with a base capable of giving sodium ions in a mixture of water and solvent to produce 3-pyridyl-1-hydroxyethylidene-1,1-bisphosphonic acid sodium hemipentahydrate of Formula (I).

2. The process according to claim 1, wherein the base used is selected from sodium methoxide, sodium ethanoate, sodium propanoate, sodium butanoate, sodium pentanoate, sodium-2-ethylhexanoate, sodium lactate, sodium acetate or mixtures thereof.

3. The process according to claim 2, wherein the base is sodium 2-ethylhexanoate.

4. The process according to claim 1, wherein the solvent used is selected from alcohol, esters, ethers, ketones, amides, nitriles or mixtures thereof, preferably alcohol.

5. The process according to claim 4, wherein the alcohol used is selected from methanol, ethanol, isopropanol.

6. The process according to claim 5, wherein the alcohol is methanol.

7. A process for the preparation of 3-pyridyl-1-hydroxyethylidene-1,1-bisphosphonic acid of Formula (III)

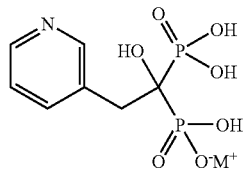

Formula III wherein M⁺ represents organic amine base which comprises reacting a compound of Formula II,

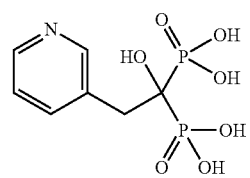

Formula II with an organic amine base in water to produce compound of Formula III.

8. The process according to claim 7, wherein the organic amine base is selected from primary amine, secondary amine, tertiary amine.

9. The process according to claim 8, wherein the organic amine base is tertiary amine.

10. The process according to claim 9, wherein the tertiary amine is selected from triethylamine, tributylamine, ethyldiisopropylamine, N-methylmorpholine, triisooctylamine, pyridine, 2,6-lutidine, quinoline, preferably triethylamine.

11. A process for the selective preparation of 3-pyridyl-1-hydroxyethylidene-1,1-bisphosphonic acid sodium in hemipentahydrate form of Formula (I),

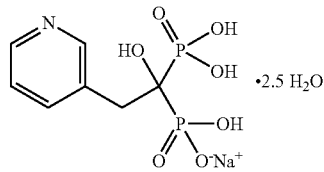

Formula I which comprises,
a) treating a compound of Formula II,

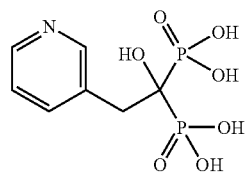

Formula II with an organic amine base in water to produce compound of Formula III,

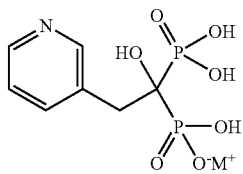

Formula III wherein M⁺ represents organic amine base, b) reacting a compound of Formula III with a base capable of giving sodium ions in a mixture of water and solvent to produce 3-pyridyl-1-hydroxyethylidene-1,1-bisphosphonic acid sodium hemi pentahydrate (I).

12. The process according to claim 11, wherein the organic amine base is selected from primary amine, secondary amine, tertiary amine.

13. The process according to claim 12, wherein the organic amine base is tertiary amine.

14. The process according to claim 13, wherein the tertiary amine is selected from triethylamine, tributylamine, ethyldiisopropylamine, N-methylmorpholine, triisooctylamine, pyridine, 2,6-lutidine, quinoline, preferably triethylamine.

15. The process according to claim 11, wherein the base used in step (b) is selected from sodium methoxide, sodium ethanoate, sodium propanoate, sodium butanoate, sodium pentanoate, sodium-2-ethylhexanoate, sodium lactate, sodium acetate or mixtures thereof.

16. The process according to claim 15, wherein the base is sodium 2-ethyihexanoate.

17. The process according to claim 11, wherein the solvent used in step b) is selected from alcohol, esters, ethers, ketones, amides, nitriles or mixtures thereof, preferably alcohol.

18. The process according to claim 17, wherein the alcohol used is selected from methanol, ethanol, isopropanol.

19. The process according to claim 18, wherein the alcohol is methanol.

* * * * *